(12) United States Patent
Zerbe et al.

(10) Patent No.: US 8,703,191 B2
(45) Date of Patent: *Apr. 22, 2014

(54) CONTROLLED-RELEASE PHARMACEUTICAL TABLETS

(75) Inventors: Horst G. Zerbe, Hudson (CA); Nadine Paiement, Montreal (CA)

(73) Assignee: Intelgenx Corp., Quebec (CA)

( * ) Notice: Subject to any disclaimer, the term of this patent is extended or adjusted under 35 U.S.C. 154(b) by 1630 days.

This patent is subject to a terminal disclaimer.

(21) Appl. No.: 11/782,838

(22) Filed: Jul. 25, 2007

(65) Prior Publication Data

US 2008/0026060 A1  Jan. 31, 2008

Related U.S. Application Data

(60) Provisional application No. 60/833,154, filed on Jul. 25, 2006.

(51) Int. Cl.
*A61K 9/22* (2006.01)

(52) U.S. Cl.
USPC ........... 424/468; 424/464; 424/469; 424/470; 424/471

(58) Field of Classification Search
None
See application file for complete search history.

(56) References Cited

U.S. PATENT DOCUMENTS

| | | | |
|---|---|---|---|
| 3,819,706 A | 6/1974 | Mehta | |
| 4,690,825 A | 9/1987 | Won | |
| 5,005,300 A | 4/1991 | Diaz et al. | |
| RE33,994 E | 7/1992 | Baker et al. | |
| 5,358,970 A | 10/1994 | Ruff et al. | |
| 5,427,798 A | 6/1995 | Ludwig et al. | |
| 5,541,231 A | 7/1996 | Ruff et al. | |
| 5,731,000 A | 3/1998 | Ruff et al. | |
| 5,763,493 A | 6/1998 | Ruff et al. | |
| 5,968,553 A | 10/1999 | Maitra et al. | |
| 6,033,686 A | 3/2000 | Seth | |
| 6,096,341 A | 8/2000 | Seth | |
| 6,120,803 A | 9/2000 | Wong et al. | |
| 6,143,327 A | 11/2000 | Seth | |
| 6,153,223 A | 11/2000 | Apelian et al. | |
| 6,162,466 A | 12/2000 | Licht et al. | |
| 6,197,827 B1 | 3/2001 | Cary | |
| 6,221,917 B1 | 4/2001 | Maitra et al. | |
| 6,242,496 B1 | 6/2001 | Kulkarni et al. | |
| 6,270,805 B1 | 8/2001 | Chen et al. | |
| 6,306,436 B1 | 10/2001 | Chungi et al. | |
| 6,333,332 B1 | 12/2001 | Han et al. | |
| 6,342,249 B1 | 1/2002 | Wong et al. | |
| 6,368,626 B1 | 4/2002 | Bhatt et al. | |
| 6,462,237 B1 | 10/2002 | Gidwani et al. | |
| 6,482,987 B2 | 11/2002 | Kulkarni et al. | |
| 6,500,459 B1 | 12/2002 | Chhabra et al. | |
| 6,548,083 B1 | 4/2003 | Wong et al. | |
| 6,652,882 B1 | 11/2003 | Odidi et al. | |
| 6,780,871 B2 | 8/2004 | Glick et al. | |
| 6,797,283 B1 | 9/2004 | Edgren et al. | |
| 6,855,334 B2 | 2/2005 | Bhatt et al. | |
| 6,893,660 B2 | 5/2005 | Li et al. | |
| 6,905,708 B2 | 6/2005 | Li et al. | |
| 7,674,479 B2 * | 3/2010 | Zerbe et al. | 424/464 |
| 2002/0048600 A1 | 4/2002 | Bhatt et al. | |
| 2003/0044462 A1 | 3/2003 | Subramanian et al. | |
| 2003/0054031 A1 | 3/2003 | Li et al. | |
| 2003/0144324 A1 * | 7/2003 | Fox et al. | 514/321 |
| 2003/0161874 A1 | 8/2003 | Li et al. | |
| 2004/0037883 A1 | 2/2004 | Zhou et al. | |
| 2004/0044005 A1 * | 3/2004 | Cary | 514/253.04 |
| 2004/0101556 A1 | 5/2004 | Li et al. | |
| 2004/0180088 A1 * | 9/2004 | Dudhara et al. | 424/471 |
| 2004/0228915 A1 * | 11/2004 | Noack et al. | 424/471 |
| 2005/0112198 A1 * | 5/2005 | Challapalli et al. | 424/464 |
| 2005/0142195 A1 | 6/2005 | Li et al. | |
| 2005/0214371 A1 | 9/2005 | Di Capua et al. | |
| 2005/0232990 A1 | 10/2005 | Boehm et al. | |
| 2005/0250838 A1 | 11/2005 | Challapalli et al. | |
| 2005/0266072 A1 | 12/2005 | Oshlack et al. | |
| 2006/0020040 A1 | 1/2006 | Chawla et al. | |
| 2006/0099260 A1 | 5/2006 | Chow et al. | |
| 2006/0165770 A1 | 7/2006 | Zhang | |
| 2006/0204571 A1 * | 9/2006 | Dhavse et al. | 424/464 |

FOREIGN PATENT DOCUMENTS

| | | |
|---|---|---|
| EP | 1 020184 | 7/2000 |
| WO | WO 95/03791 | 2/1995 |
| WO | WO 00/21504 | 4/2000 |
| WO | WO 01/80824 | 11/2001 |
| WO | WO 03/086362 | 10/2003 |
| WO | WO 2004/047809 | 6/2004 |
| WO | WO 2004/087175 | 10/2004 |
| WO | WO 2004110422 | 12/2004 |
| WO | WO 2005077332 A2 * | 8/2005 |
| WO | WO 2005/092297 | 10/2005 |

* cited by examiner

*Primary Examiner* — James Rogers

(74) *Attorney, Agent, or Firm* — Butzel Long

(57) ABSTRACT

Controlled-release tablets exhibiting excellent storage stability are achieved by granulating a pharmaceutically active agent with a hydroxyalkylceluose, blending the resulting granules with an extragranular phase composed of a particulate material that provides a sustained-release matrix, and compressing the blend into a tablet form, which may be optionally coated, such as with an enteric coating composition, to provide delayed release and/or to enhance stability of the active agent.

10 Claims, No Drawings

CONTROLLED-RELEASE PHARMACEUTICAL TABLETS

CROSS-REFERENCE TO RELATED APPLICATION

This application claims priority under 35 U.S.C. §119(e) on U.S. Provisional Application No. 60/833,154 entitled STABILIZED SUSTAINED-RELEASE BUPROPION AND BUPROPION/MECAMYLAMINE TABLETS, filed Jul. 25, 2006 the entire disclosure of which is incorporated herein by reference.

FIELD OF THE INVENTION

This invention relates to pharmaceutical dosage forms, and more particularly to controlled-release tablets.

BACKGROUND OF THE INVENTION

Bupropion is used as an antidepressant. It has also been used either alone or in combination with other drugs as a smoking cessation aid. Bupropion is highly hygroscopic and susceptible to decomposition. Various techniques have been employed to overcome the stability issues with bupropion. These techniques have included combining bupropion hydrochloride with a stabilizing agent, typically a pharmaceutically acceptable acid, e.g., hydrochloric acid, phosphoric acid, nitric acid, sulfuric acid, malic acid, citric acid, tartaric acid, ascorbic acid, isoascorbic acid, etc. Other attempts to stabilize bupropion hydrochloride in pharmaceutical dosage forms include application of coating films or barriers, either on the bupropion hydrochloride or on excipients utilized in preparation of bupropion hydrochloride pharmaceutical dosage forms. It has also been proposed to stabilize bupropion hydrochloride in pharmaceutical dosage forms by forming complexes between the bupropion hydrochloride and an ion exchange resin, or by occluding the bupropion hydrochloride with cyclodextrin. Others have reported that bupropion hydrochloride is stable by itself under normal storage conditions, but can easily degrade in the presence of conventional excipients used in commercial formulations. It has been theorized that small amounts of impurities in the excipients, typically residual impurities such as peroxides, superoxides, hypochlorites and formic acid introduced during the manufacturing processes, can interact with the bupropion hydrochloride to cause decomposition during storage. Accordingly, it has been proposed that one possible strategy to eliminate or reduce decomposition of bupropion hydrochloride in pharmaceutical dosage forms is to pretreat the excipients to remove or neutralize impurities that can induce oxidation, add chelating agents to formulations to prevent metal induced oxidation, and/or add antioxidants such as L-cysteine hydrochloride to pharmaceutical dosage forms containing bupropion hydrochloride.

Commercially available sustained-release oral formulations of bupropion hydrochloride have been prepared by mixing the bupropion hydrochloride with a stabilizing agent and with various celluloses, alkyl celluloses and hydroxyalkylcelluloses, carboxyalkylcelluloses, polyalkylene glycols and acrylic acid polymers. It has also been proposed that complexes formed between bupropion hydrochloride and an ion exchange resin may be used for achieving a sustained-released effect.

The utility of pharmaceutical therapies and compositions involving the combination of mecamylamine hydrochloride and bupropion hydrochloride in the treatment of tobacco addiction or nicotine addiction, for palliating nicotine withdrawal symptoms, and/or facilitating smoking sensation is disclosed in U.S. Pat. No. 6,197,827, which is incorporated by reference in its entirety herein. This patent generally describes the concept of administering mecamylamine and bupropion either individually or in a single tablet, but does not disclose any particular formulation, or provide details as to how stable sustained-release tablet formulations comprising a therapeutically effective combination of mecamylamine hydrochloride and bupropion hydrochloride can be prepared. There is only a relatively general suggestion that time-release formulations may be prepared "as is known in the art and disclosed in U.S. Pat. Nos. 4,690,825 and 5,005,300," and that "conventional means with pharmaceutically acceptable excipients such as binding agents . . . ; fillers . . . ; disintegrants . . . ; or wetting agents . . . ; glidants, artificial and natural flavors and sweeteners; artificial or natural colors and dyes; and stabilizers" may be employed. This teaching does not recognize potential interactions between mecamylamine hydrochloride and bupropion hydrochloride, and does not address the known stability issues with bupropion hydrochloride.

SUMMARY OF THE INVENTION

In accordance with an aspect of this invention, an alternative solution to providing controlled release of a pharmaceutically active agent in a tablet dosage form is provided. In accordance with this aspect of the invention, a granulation comprising a pharmaceutically active agent is distributed in a sustained-release matrix. More particularly, the pharmaceutical tablets in accordance with this aspect of the invention comprise a granular phase composed of a pharmaceutically active agent, and a hydroxyalkylcellulose. The granular phase is distributed within an extragranular phase comprising a particulate material that provides a sustained-release effect, such as by providing a diffusion barrier and/or controlled erosion.

In accordance with a related aspect of the invention, a controlled-release pharmaceutical tablet is prepared by granulating a pharmaceutically active agent with a hydroxyalkylcellulose. The resulting granulation is dried to an acceptable moisture content, and the dried granulation may optionally be milled and/or screened to achieve a desired granulation particle size. Thereafter, the dried granulation is dry blended with a particulate material capable of forming a sustained-release matrix in which the granules are distributed. The resulting blend is then compressed into a tablet form.

In accordance with another aspect of the invention, there is provided a single tablet dosage form providing controlled release of both bupropion and mecamylamine in which the bupropion is stabilized against decomposition, and bupropion and mecamylamine are stabilized against interactions with each other. More particularly, the invention provides a combination controlled-release bupropion, controlled-release mecamylamine pharmaceutical tablet in which mecamylamine and a bupropion granulation are distributed in an extragranular phase comprising a particulate material capable of providing a controlled-release matrix.

In accordance with a related aspect of the invention, a combination controlled-release bupropion, controlled-release mecamylamine pharmaceutical tablet is prepared by granulating bupropion with a hydroxyalkylcellulose and an optional pharmaceutically acceptable stabilizing agent; drying the bupropion granulation; optionally milling and/or screening the dried granulation; dry blending the dried granulation with mecamylamine or mecamylamine granules; blending the combined granulations of bupropion and mecamylamine with a suitable extragranular phase; and compressing the resulting blend into a tablet form.

These and other features, advantages and objects of the present invention will be further understood and appreciated by those skilled in the art by reference to the following specification and claims.

DETAILED DESCRIPTION OF THE PREFERRED EMBODIMENTS

In accordance with the various embodiments of the invention, a pharmaceutically active agent is incorporated in a granular phase that is distributed within an extragranular phase which provides a sustained-release matrix for the active agent.

The invention is illustrated herein with respect to bupropion and/or mecamylamine. However, the invention has broad application in the formulation of dosage forms for achieving controlled release of a variety of pharmaceutically active agents, particularly those that are susceptible to hydrolytic degradation. It is further contemplated that the invention may have utility for administering one or more pharmaceutically active agents in which one or more of the active agent(s) is available, at least in part, in an immediate release form.

The term "bupropion" is, unless otherwise indicated, intended to encompass bupropion in its base form, as well as various acid addition salts of bupropion, including bupropion hydrochloride, and enantiomers thereof in either pure form or in any ratio. Conventional wet granulation techniques may be employed for preparing the stabilized bupropion granules. The terms "granule", "granulation" and "granular phase" refer to particulate agglomerates or aggregates, such as those formed by combining the components of the granulation in the presence of a liquid to bind individual particles into aggregated clumps or clusters comprising the individual components of the granulation. Depending on the granulation techniques employed, the selected ingredients, and the desired release properties, the granules, after being dried, can be milled and/or sieved to achieve a desired granule size.

The term "therapeutically effective amount" refers to an amount of a pharmaceutically active agent, which when administered to a particular subject, considering the subject's age, weight and other relevant characteristics, will attenuate, ameliorate, or eliminate one or more symptoms of a disease or condition that is treatable with the pharmaceutically active agent.

The term "controlled release" is meant to encompass delayed and/or sustained release.

Suitable optional bupropion stabilizing agents may be selected from those known in the art, including various inorganic acids, such as hydrochloric acid, phosphoric acid, nitric acid, and sulfuric acid, organic carboxylic, dicarboxylic and polycarboxylic acids such as malic acid, citric acid, tartaric acid, ascorbic acid, isoascorbic acid, oxalic aid, succinic acid, adipic acid, fumaric acid, benzoic acid, and phthalic acid; sulfites such as sodium metabisulfite and potassium metabisulfite; and organic esters such as L-ascorbic acid palmitate. Other examples of bupropion stabilizers include L-cystine dihydrochloride, L-cysteine hydrochloride, and glycine hydrochloride. Preferred bupropion stabilizing agents include generally any pharmaceutically acceptable acid that maintains the granulated bupropion at an acidic pH when contacted with water. In general, suitable acids include those that lower the pH of an aqueous solution to a value in the range from about 0.5 to about 4.0 when added to the neutral solution at a concentration of about 0.003 parts by weight to 100 parts by weight of the solution. An example of a suitable acidic neutralizer for bupropion hydrochloride is hydrochloric acid.

Suitable hydroxyalkylcellulose polymers that may be employed for preparing the bupropion granulation include hydroxymethycellulose, hydroxyethylcellulose, and hydroxypropylcellulose. The term "hydroxyalkylcellulose" is also intended to encompass hydroxypropylmethylcellulose.

The amount of bupropion may be selected to provide conventional therapeutic amounts in the range from about 25 milligrams to about 500 milligrams, such as 50, 75, 100, 150, 225, and 450 milligrams.

Surprisingly, the amount of hydroxyalkylcellulose needed in the bupropion granules to achieve effective stabilization of the bupropion in the tablet dosage forms of the invention, and to prevent degradative interactions between bupropion and mecamylamine for tablets containing these two pharmaceutically active compounds, is relatively low. The term "mecamylamine" is, unless otherwise indicated, intended to encompass mecamylamine in its base form, as well as acid addition salts of mecamylamine, including mecamylamine hydrochloride, and enantiomers and/or diastereomers thereof, in either pure form or in any ratio. Typically, a suitable and effective amount of hydroxyalkylcellulose in the granular phase is from about 10 to about 30% by weight of the granular phase, with the remaining 70% to 90% of the weight of the granular phase being primarily bupropion, the stabilizing component typically comprising substantially less than 1% by weight of the bupropion granular phase. The preferred hydroxyalkylcellulose is hydroxypropylcellulose. Other excipients and/or adjuvants may be present in the granular phase, typically in relatively minor amounts, if at all.

For sustained-release bupropion tablets which do not contain mecamylamine, the relative amount of granular phase to extragranular phase may vary considerably, depending on the selected tablet dose and the desired release properties. However, the granular phase typically and generally comprises 30% to 70% of the combined weight of the granular phase and the extragranular phase. In the case of tablets providing both sustained release of bupropion and mecamylamine, the mecamylamine need not, but may be granulated with a hydroxyalkylcellulose, preferably hydroxypropylcellulose, to effectively reduce or eliminate potential interactions between bupropion and mecamylamine. However, because pharmaceutically effective doses of mecamylamine are substantially lower than those of bupropion, the total amount of bupropion granules and mecamylamine granules (when mecamylamine is incorporated into the dosage form in a granular phase) may be in a range of from about 30% to about 75% of the combined weight of the two granular phases and the extragranular phase.

Therapeutically effective amounts of mecamylamine are well known in the art, and generally range from about 1 to about 10 milligrams per tablet, with specific examples being 3 milligrams, 6 milligrams, and 9 milligrams.

The extragranular phase may be comprised of generally any particulate material that can be compressed into a tablet form and that provides a sustained-release matrix. Materials having suitable sustained-release properties are generally well known in the art, and typically provide sustained release by providing a diffusion barrier for the active or active ingredients and/or by eroding at a desired controlled rate, with the result being a relatively uniform or constant rate of release of the active ingredient or active ingredients over an extended period of time, such as 4, 8, 16 or 24 hours. Such sustained release is desirable for maintaining therapeutically effective blood plasma levels of the drug over an extended period of time without requiring administration of multiple tablets over the extended period. Examples of suitable extragranular particulate materials that may be used for providing a sustained-release matrix include poly(vinylacetate), polyvinylpyrrolidone, blends of poly(vinylacetate) and polyvinylpyrrolidione, copolymers of vinylpyrrolidone such as copolymers of vinylacetate and vinylpyrrolidone, polyethylene oxides, modified starches, and hydroxyethylcellulose.

The extragranular phase may also contain small amounts of conventional additives such as colorants, opacifiers, glidants, etc.

Suitable extragranular excipients include water-swellable and/or water-erodible polymers, with suitable examples including polyvinylpyrrolidone, poly(vinylacetate), copolymers of vinylpyrrolidone and vinylacetate and blends thereof. The blends may further comprise a polyalkylene oxide, such as polyethylene glycol, in an amount effective to adjust the hydrophilicity of the sustained-release matrix provided by the extragranular phase, and thereby adjust the rate of sustained release.

In addition to sustained release, it may be desirable to provide bupropion and bupropion/mecamylamine tablet dosage forms having delayed-release properties. The term "delayed release" as used herein refers to release of the pharmaceutically active compound or compounds that is delayed until after the dosage form has passed through the stomach and into the intestine. As is well known in the art, such delayed-release can be achieved by coating the compressed tablet with a polymer coating composition that remains intact in the upper part of the gastrointestinal tract while in contact with acidic gastric fluids, but which readily decomposes or solubilizes at the higher pH in the intestine, i.e., an enteric coating.

It may be beneficial to incorporate a lubricant in the extragranular phase to aid tableting. While common tableting lubricants such as magnesium stearate may be employed, it has been discovered that stearic acid, in addition to providing the desired lubricating effect, also imparts enhanced storage stability to the resulting tablets.

The enteric coating generally comprises components soluble in a liquid at a pH of about 5 or more and includes components that impart resistance to gastric conditions, as is known in the art. Some examples of the components for an enteric coating include anionic acrylic resins, such as methacrylic acid/methyl acrylate copolymer and methacrylic acid/ethyl acrylate copolymer (for example, Eudragit® L, Eudragit® S (Rohm, Germany), hydroxypropylmethylcellulose acetate succinate, hydroxypropylmethylcellulose phthalate, cellulose acetate phtalate, carboxymethylcellulose acetate phthalate, shellac and so forth. Mixtures of those compounds also may be used. The enteric coating can comprise from about 1 to about 10% of the combined weight of the tablet.

Other auxiliary components such as a minor amount of a plasticizer, such as acetyltributylcitrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol, propylene glycol and mixtures thereof in combination with an antisticking agent which may be a silicate such as talc, can be used. Titanium oxide also can be included in the coating, as well as known cellulosic materials. A flavorant or colorant may be included. The auxiliary components may be added to the enteric coating composition in combination with appropriate solvents.

It has been surprisingly discovered that bupropion can be effectively stabilized by developing a sufficiently thick or complete enteric coating on a compressed tablet core containing bupropion. In particular, it has been discovered that an enteric coating that constitutes at least 6% of the weight of the compressed tablet core containing bupropion substantially reduces or eliminates hydrolytic degradation of bupropion during storage at room temperature for 6 months. Higher levels such as 10% of the weight of the core may be used. It is believed that a stabilizing effect is surprisingly achieved, either with or without a stabilizing agent in the compressed tablet core containing bupropion, when a suitably thick and/or complete enteric coating is applied to the core. Further, it is believed that a stabilizing effect is achieved using a suitably thick or complete enteric coating regardless of whether the core comprises a granular and extragranular phase as described herein with respect to other aspects of the invention, or comprises a more conventional compressed tablet core, with or without mecamylamine.

The following examples are illustrative of the invention, but do not define the limits of the invention.

EXAMPLE 1

Examples of formulations for sustained-release bupropion hydrochloride tablets and bupropion hydrochloride/mecamylamine hydrochloride tablets are summarized in the following Table 1. The tablets were made using a wet granulation method where 0.3N HCl was used as the granulation liquid. The active and HPC were homogenized for two minutes in a high shear mixer. The mixer was set at 500 rpm and the chopper motor was set at 1000 rpm. The bupropion wet granules were air dried briefly and then passed through a 2.36 mm sieve and then through a 1.18 mm sieve. The wet granulation of mecamylamine was performed with water. The mecamylamine wet granules were dried overnight at 50° C. and then passed through a 1.18 mm sieve. The one or two granules were blended and then mixed with Kollidon SR and polyethylene oxide previously passed through a 0.60 mm sieve. All excipients were blended for 5 minutes in a V blender. Following the addition of lubricant and other excipients, blending was continued for another minute. The tablet was compressed on a rotary press. The tablets were coated using a solution of Eudragit® L30D-55 and other additives as shown in Table 2. The coating was applied using a fluid bed drier at a temperature of 40° C. at 0.8 bar, with a flow rate of 2.5 g/min, to provide a weight gain of 4%. The illustrated exemplary tablet formulations (1-5) prevent potential interactions between bupropion hydrochloride and mecamylamine hydrochloride for those tablets containing both active ingredients in a single tablet dosage form. The tablet were stable, which means that at least 80% of the initial potency of the bupropion hydrochloride in each tablet was maintained after storage for at least 10 weeks at 40° C. and 75% relative humidity.

TABLE 1

Bupropion/Mecamylamine Current Formulation (Dry Basis)

| Dosage Bupropion/Mecamylamine (mg) Weight (mg per tablet) | Example 1A | 1B | 1C | 1D | 1E |
|---|---|---|---|---|---|
| Active Granulations: | | | | | |
| Bupropion HCl | 225.00 | 225.00 | 225.00 | 225.00 | 450.00 |
| Hydroxypropylcellulose Klucel GXF | 40.00 | 40.00 | 40.00 | 40.00 | 80.00 |
| 0.3 N Hydrochloric acid | | | | | |
| Mecamylamine HCl | — | 3.00 | 6.00 | 9.00 | — |
| Hydroxypropylcellulose Klucel GXF | — | 0.67 | 1.33 | 2.00 | — |
| Water | | | | | |
| External phase: | | | | | |
| Poly(vinylacetate) povidone blend Kollidon SR | 101.00 | 101.00 | 101.00 | 101.00 | 101.00 |
| Polyethylene oxide N60K | 58.00 | 58.00 | 58.00 | 58.00 | 58.00 |
| Stearic acid | 7.50 | 7.50 | 7.50 | 7.50 | 7.50 |
| Colloidal silicon dioxide | 2.50 | 2.50 | 2.50 | 2.50 | 2.50 |
| Coating: | | | | | |
| Methacrylic acid copolymer dispersion | 10.42 | 10.50 | 10.63 | 10.68 | 16.84 |
| Talc | 4.17 | 4.20 | 4.21 | 4.27 | 6.67 |
| Polyethylene glycol 8000 | 1.39 | 1.40 | 1.40 | 1.42 | 2.22 |
| Titanium dioxide | 1.04 | 1.05 | 1.05 | 1.07 | 1.67 |
| Carboxymethylcellulose sodium Hercules 7LF | 0.35 | 0.35 | 0.35 | 0.36 | 0.56 |
| Water | | | | | |
| Total Tablet weight (mg) | 451.37 | 455.17 | 458.97 | 462.80 | 726.96 |

EXAMPLE 2

A tablet containing 225 mg of bupropion as provided in Example 1A was compared to Wellbutrin XL 150 in a dissolution study using USP 26 App. (basket) or the two paddle test for extended release tablets. In the paddle test, at 50 rpm, the tablets were exposed to two paddles in 900 ml of water for 8 hours. In the basket test, tablets were exposed to 0.1 N HCl for two hours to mimic gastric conditions. After the two hours, the tablets were moved to simulated intestinal fluid at pH 6.8 at 100 rpm for 22 hours. At one hour time points throughout the incubation in the basket or paddle tests, beginning at time 0, a fluid sample was obtained and tested for presence and amount of bupropion. The simulated intestinal fluid (SIF) comprises 0.05 M tris hydroxymethylaminomethane adjusted to pH 6.8 with 2N sodium hydroxide solution.

Throughout the 24 hour period, at the 24 hour time point, all tablets had released about 95% of the bupropion dose contained in the tablet, the tablet of the instant invention released nearly the same percentage of bupropion as did the name brand product, including a two hour lag at the onset wherein essentially no bupropion was released from the tablets.

The same results were obtained with tablets containing 450 mg of bupropion. In one set of experiments, some tablets did not contain an enteric coating. That tablet released about 45% of the carried bupropion at the two hour time point, and about 70% at the four hour time point. In another set of experiments, two other tablets with 450 mg of bupropion contained a 4.68% enteric coating. One tablet also included a lubricant, magnesium stearate, in the formulation. Both of those tablets demonstrated a nearly identical dissolution profile as observed for Wellbutrin XL 150. In this set of experiments, the initial two hour incubation was done not in 0.1; N HCl but in simulated gastric fluid (SGF) which comprises 12 g of sodium chloride and 42 ml of hydrochloric acid, diluted to 6 liters and pH adjusted to 1.2.

EXAMPLE 3

Stability of bupropion HCl 225 mg extended release tablets and release profile were examined. Tablets were made as described in Example 1. Tablets were then stored at two different conditions, 25° C./60% RH and 40° C./75% RH. Samples were obtained at 0 and 1 month, and for the lower temperature regimen, also at 3 months, and then tested for bupropion, content uniformity, dissolution and related compounds. The results were compared to the specification of related approved drugs.

Throughout the lower temperature regimen, the instant tablets conformed with the standard parameters. At the higher temperature regimen, the instant tablets conformed at the 0 and one month sampling periods.

EXAMPLE 4

In vitro dissolution was compared to in vivo absorption, the amounts absorbed in vivo were calculated using the Wagner/Nelson method and plotted against the amounts released in vitro at equivalent time points using a Levy plot, practicing known methods. The tablet of interest contained 225 mg of bupropion, and was compared to Wellbutrin XL 300 mg.

Selected patients screened to meet parameters established in the approved protocol at a VA hospital, were provided with a single tablet after a nine hour fast. Blood samples were obtained, serum separated and the amount of bupropion was determined by liquid chromatography and mass spectrometry. A blood sample was also take prior to administration of the tablet.

Over a 36 hour period, nearly 100% of the bupropion was absorbed. The two hour lag period was noted. Overall, the profiles were the same, with the instant tablet identical to the Wellbutrin up through six hours, and then demonstrating an absorption profile that paralleled that of Wellbutrin, although at a level about 5% lower. The Wagner/Nelson method used assumes a one compartment, one body model for the drug. On the other hand bupropion has been reported to follow a two compartment, one body model. The Lou Riegelman method provides a suitable two compartment model. Nevertheless, the Wagner/Nelson method provides a sufficiently accurate approximation of the true absorption profile.

The Levy plots were substantially identical, the data best fit a second degree polynomial relationship. Hence, the absorption of the drug is nearly quantitative during the first eight hours after administration but is reduced as the dosage form enters the lower parts of the intestine. The pattern was observed for both Wellbutrin and the instant tablet. Thus, the absorption rate is dependent on the drug and not on the dosage.

The overall amount of drug released was about 5% lower than that of Wellbutrin. However, the maximum concentration was the same and was obtained at the same time.

EXAMPLE 5

Tablet cores are prepared as described above in Example 1A, and subsequently coated with an enteric coating solution having the formula set forth in the following Table 2.

TABLE 2

| Coating solution | |
|---|---|
| Eudragit ® L30 D55 (305 Dispersion) | 39.76% |
| Talc | 4.77% |
| Polyethylene glycol 8000 | 1.59% |
| Titanium dioxide | 1.20% |
| Carboxymethyl cellulose sodium | 0.40% |
| Water | 52.28% |
| Solid percentage | 20% |
| Polymer percentage | 12% |

Conventional coating techniques are employed to develop a dried coating on the compressed tablet cores that has a weight per tablet equal to either 4% or 6% of the weight of the tablet cores. Samples of the coated tablets are initially analyzed for the hydrolytic degradation product m-chlorobenzoic acid, and samples are subsequently analyzed after storage at room temperature for 6 months. The results show that the tablets (both 4% and 6% coatings) do not initially contain a quantifiable amount of m-chlorobenzoic acid (e.g., less than 0.05% based on the total weight of bupropion hydrochloride). After 6 months of storage at room temperature, the tablets (4 batches) with a 4% coating (weight of coating as a percentage of the weight of the compressed tablet core prior to coating) exhibit a small amount of degradation. More specifically, 0.1 to 0.3% conversion of bupropion hydrochloride to m-chlorobenzoic acid is found. Accordingly, a 4% coating appears to provide marginally acceptable stability for 6 months. The USP requirement is no more than 0.3%. Tablets (4 batches) having the 6% coating (weight of the coating as a percentage of the weight of the compressed tablet core) did not exhibit any quantifiable degradation (as characterized by quantitative analysis for m-chlorobenzoic acid) after 6 months of storage at room temperature.

The above description is considered that of the preferred embodiments only. Modifications of the invention will occur to those skilled in the art and to those who make or use the invention. Therefore, it is understood that the embodiments described above are merely for illustrative purposes and not intended to limit the scope of the invention, which is defined by the following claims as interpreted according to the principles of patent law, including the doctrine of equivalents.

The invention claimed is:

1. A controlled-release pharmaceutical tablet comprising:
a first granular phase including bupropion, an acidic stabilizing agent in an amount less than 1% of the weight of the first granular phase, and hydroxypropylcellulose in an amount of from about 10% to about 30% of the weight of the first granular phase;
a second granular phase comprising mecamylamine and a hydroxyalkylcellulose; and
an extragranular phase that provides a sustained-release matrix, the first and second granular phases are dispersed in the extragranular phase, the extragranular phase comprising a particulate material that provides a diffusion barrier, controlled erosion, or a diffusion barrier and controlled erosion, wherein the extragranular phase includes polyalkylene oxide and a water-swellable or water-erodible polymer selected from the group consisting of polyvinyl pyrrolidone, poly(vinylacetate), copolymers of vinylpyrrolidone and vinylacetate, and blends thereof, the extragranular phase comprising polyalkylene oxide in an amount that is effective to adjust hydrophilicity of the sustained-release matrix and thereby adjust the rate of sustained release;
wherein the first granular phase comprises about 30% to about 70% of the combined weight of the first granular phase and the extragranular phase.

2. The tablet of claim 1, in which bupropion comprises from 70% to 90% of the weight of the first granular phase.

3. The tablet of claim 1, wherein the acidic stabilizing agent is hydrochloric acid.

4. The tablet of claim 1, further comprising an enteric coating.

5. The tablet of claim 1, in which the extragranular phase comprises a blend of polyvinylpyrrolidone, poly(vinylacetate), and polyethylene oxide.

6. The tablet of claim 1, in which the extragranular phase comprises a copolymer of vinylpyrrolidone and vinylacetate.

7. The tablet of claim 6, wherein the polyalkylene oxide is polyethylene oxide.

8. The tablet of claim 1, wherein the extragranular phase includes stearic acid in an amount that is effective to provide lubrication during tableting.

9. A combination controlled-release bupropion, controlled-release mecamylamine pharmaceutical tablet comprising:
a granular phase comprising bupropion, hydroxypropylcellulose in an amount of from about 10% to about 30% of the weight of the granular phase;
a pharmaceutically effective amount of mecamylamine; and
an extragranular phase comprised of a particulate material that provides a sustained-release matrix, the granular phase and the mecamylamine being dispersed within the extragranular phase, the extragranular phase comprising a particulate material that provides a diffusion barrier, controlled erosion, or a diffusion barrier and controlled erosion, wherein the extragranular phase includes polyalkylene oxide and a water-swellable or water-erodible polymer selected from the group consisting of polyinyl pyrrolidone, poly(vinylacetate), copolymers of vinylpyrrolidone and vinylacetate, and blends thereof, the extragranular phase comprising polyalkylene oxide in an amount that is effective to adjust hydrophilicity of the sustained-release matrix and thereby adjust the rate of sustained-release, and wherein the granular phase comprises about 30% to about 70% of the combined weight of the granular phase and the extragranular phase.

10. The tablet of claim 9, in which the granular phase further comprises a pharmaceutically acceptable bupropion stabilizer.

* * * * *